United States Patent

Menzi et al.

[11] Patent Number: 5,237,825
[45] Date of Patent: Aug. 24, 1993

[54] METHOD AND APPARATUS FOR CRYOGENICALLY COOLING SAMPLES

[75] Inventors: Werner Menzi, Maynard; Emil S. Koteles, Lexington, both of Mass.

[73] Assignee: GTE Laboratories Incorporated, Waltham, Mass.

[21] Appl. No.: 791,750

[22] Filed: Nov. 8, 1991

[51] Int. Cl.$^5$ ............................................. F25B 19/00
[52] U.S. Cl. ................................. 62/51.1; 62/55.5; 62/49.1
[58] Field of Search ....................... 62/51.1, 55.5, 49.1

[56] References Cited

U.S. PATENT DOCUMENTS

| | | | |
|---|---|---|---|
| 4,718,241 | 1/1988 | Lessard | 62/55.5 |
| 4,848,093 | 7/1989 | Simmonds et al. | 62/49.1 |
| 4,872,321 | 10/1989 | Buchanan | 62/51.1 |
| 4,896,511 | 1/1990 | Lessard | 62/55.5 |

Primary Examiner—Allen J. Flanigan
Attorney, Agent, or Firm—Victor F. Lohmann, III

[57] ABSTRACT

An apparatus for cryogenically cooling a sample comprises a sample chamber within which the sample is suspended, and a vacuum chamber enclosing the sample chamber. A cryogenic element forms at least part of the sample chamber and is in spaced-apart relation to the sample. The element is maintained at cryogenic temperatures by a gas cryopump. A sufficient amount of heat-conductive gas is introduced into the sample chamber for placing the sample in thermal communication with the cryogenic element, thereby cooling the sample to cryogenic temperatures.

6 Claims, 1 Drawing Sheet

METHOD AND APPARATUS FOR CRYOGENICALLY COOLING SAMPLES

FIELD OF THE INVENTION

This invention relates to a cooling apparatus and, more particularly, to an apparatus for cryogenically cooling samples in a chamber.

BACKGROUND OF THE INVENTION

It is often necessary to maintain samples such as electronic devices at very cold temperatures approaching absolute zero. For example, certain electronic devices must operate at low cryogenic temperatures of about 4 K to reduce electronic noise resulting from thermal fluctuations in circuits, and induce a superconducting state in electronic components. Cryogenic temperatures are also sometimes required to slow the rate of chemical reactions.

A conventional apparatus for lowering the temperature of samples to cryogenic levels employs cryostats which immerse the samples in cryogenic liquids such as nitrogen and helium to reach temperatures of −321° F. and −452° F., respectively. The use of such liquids, however, is complex, hazardous, expensive, and time-consuming. An example of a conventional immersive system is described in U.S. Pat. No. 4,848,093, which discloses a method of regulating the temperature of a cryogenic test chamber by controlling the flow of externally-supplied liquid helium.

Another conventional apparatus utilizing cryogenic liquids includes a dual chamber configuration with an inner chamber for housing a sample and an outer chamber enclosing the inner chamber. Liquid helium flows through the interior of a copper block exposed to the sample to cool the inner chamber.

A further conventional assembly employs cryostats using a closed cycle liquid helium generator as a cryopump to achieve non-immersive cooling with "cold finger" contact. Although cryopumps eliminate the need for cryogenic liquids, these systems introduce unacceptable strain into a sample as it is being cooled down from room temperature because the sample must physically contact the cooling element otherwise known as the "cold finger."

U.S. Pat. No. 4,872,321 addresses the problem of rigidly attaching devices to the cold finger of a cryopump in an evacuated sample chamber. As noted in U.S. Pat. No. 4,872,321, the stretching of tubing within a cryogenic precooler as gas is being cycled produces significant vibrational amplitudes at the cold finger which are transmitted directly to the devices/samples being cooled.

U.S. Pat. No. 4,872,321 teaches that the transmission of this vibrational amplitude to the devices can be prevented by mounting the devices from an independent support which is mechanically isolated from the portion of the precooler that is subject to the stretching vibration, namely the cold finger and adjacent portions of the precooler. Flexible coupling means, which connect the cold finger to the independent sample support through both a cryogenic gas supply and return line, specifically prevent transmission of stretching vibrations from the cold finger to the sample support and devices.

However, although mechanical coupling is reduced (but not eliminated) between the cold finger and the devices, vibrations from the piston or displacer in the cryopump are still transmitted to the device, and strain appears in the sample due to differences in the thermal expansion coefficients of the devices and cold finger.

OBJECTS OF THE INVENTION

It is a principal object of the present invention to overcome the above-cited and other disadvantages of the prior art.

It is a further object of the present invention to provide a method and apparatus for cryogenically cooling a sample which is physically isolated from a cryogenic element.

It is a yet further object of the present invention to cryogenically cool samples with an exchange gas to prevent strain in the samples.

SUMMARY OF THE INVENTION

The present invention is directed to an apparatus for cryogenically cooling a sample. The apparatus comprises a sample chamber, means for suspending the sample within said sample chamber, a vacuum chamber enclosing the sample chamber, a cryogenic element forming at least part of said sample chamber and in spaced-apart exposed relation to the sample, cooling means for maintaining said element at cryogenic temperatures, and means for introducing a sufficient heat conductive gas at a pressure into the sample chamber to place the sample in thermal communication with the cryogenic element. The gas communicates heat from the sample to the cryogenic element such that the sample is cryogenically cooled without experiencing strain.

A method of cryogenically cooling a sample comprises the steps of suspending the sample in a sample chamber having a thermally-conductive element as part of the chamber, thermally insulating the sample chamber, maintaining the element at cryogenic temperatures, evacuating the sample chamber, admitting gas into the evacuated sample chamber through a gas inlet of the sample chamber, and sealing the inlet after a sufficient amount of gas is present in the chamber such that the sample is in thermal communication with the element.

BRIEF DESCRIPTION OF THE DRAWINGS

The sole FIGURE shows a cooling apparatus in accordance with a preferred embodiment of the present invention.

DETAILED DESCRIPTION OF THE PREFERRED EMBODIMENTS

Figure 1:
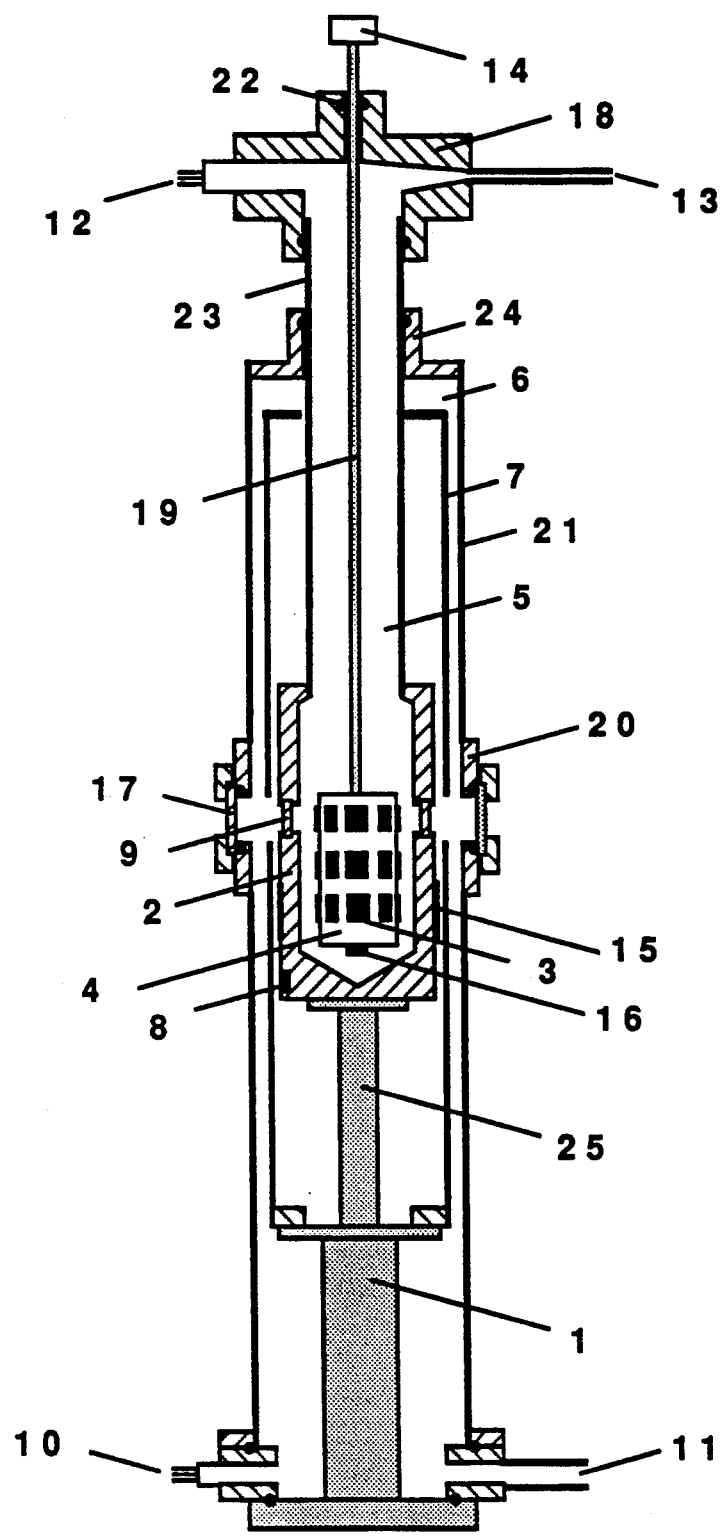

The present invention permits the cryogenic cooling of a sample with an exchange gas to avoid physical contact with the cold finger of a cryogenic pump, thereby eliminating the strain exhibited by samples in conventional cryogenic cooling apparatus.

In accordance with the present invention, a cryogenic cooling apparatus includes an inner sample chamber and a surrounding outer vacuum chamber for thermally insulating the sample chamber from outside temperatures. This inner chamber is constructed to have a cryogenic element in the interior of the inner chamber so that the sample environment is exposed to the cryogenic temperatures of the element.

A sample is supported within the chamber in spaced-apart relation to the element, and a source of heat-conductive gas, preferably helium, is coupled to the input port for introducing gas into the chamber for cooling to helium temperatures (less than 80K). The admitted gas ventilates and draws heat from the sample, thereby facilitating a transfer of heat from the sample to the cryogenic element. The element is maintained at a cryogenic temperature by being in contact with the cold finger of a cryopump.

Preferably, the cryopump used in the present invention does not require liquid cryogenic coolants, but employs a Joule-Thompson cycle for continually compressing and expanding a gas to provide a cryogenically cooled gas which cools the attached cold finger.

The sole FIGURE details a cryogenic apparatus constructed in accordance with the present invention. This apparatus is for illustrative purposes only, and should not serve as a limitation of the present invention as it should be apparent to those skilled in the art that other modifications can be made within the scope of the present invention.

As shown in the apparatus of the FIGURE, a set of samples 3 placed on a holder 4 is supported by an insulated rod 19 in a sample chamber 5. The apparatus includes a cryopump 1 whose cold finger 25 is adapted to support and is in thermal contact with a copper block 2 defining a lower portion of sample chamber 5. The block 2 is attached to the upper portion of chamber 5 with solder contacts. This upper portion of chamber 5 preferably has a cylindrical geometry, but it should be obvious to those skilled in the art that other geometries are possible. The chamber 5 is adapted to receive an exchange gas through inlet 13, and is sealed from the external environment with O-ring seals 22.

The apparatus includes an outer chamber or jacket 6 enclosing the inner sample chamber 5 which, as noted before, contains the samples to be studied and is to be maintained at cryogenic temperatures. The jacket 6 is evacuated through a vacuum port 11 at a lower end of the apparatus and is kept at a high vacuum in order to thermally insulate the sample chamber 5 from room temperature. Otherwise, the outer walls of the sample chamber would experience frosting, and low cryogenic temperatures would not be reached in sample chamber 5.

The apparatus preferably includes a highly conductive metallic shield 7, called a cryoshroud, to facilitate insulation of the sample chamber from outside temperatures. Accordingly, the shield is kept at an intermediate temperature in order to reduce the heat load on the sample chamber 5 from the outer wall 21 of the vacuum jacket 6. An O-ring seal 24 at an upper end of the vacuum jacket 6 is used to seal the vacuum jacket 6 from the outside environment in order to facilitate quick and easy dismantlement of the two vacuum chambers for ease of cleaning and repair.

The temperature of the copper block 2 in sample chamber 5 is monitored with a temperature sensor 8 which has leads coming from an electrical vacuum feedthrough 10 on a lower end of the apparatus. This feedthrough 10 also facilitates the connection of electrical power leads to the heater 15 mounted on the copper block 2 for varying the temperature of the copper block 2 and thus the exchange gas, and finally the samples 3.

A principal advantage of the apparatus in the FIGURE is that the samples can be mounted strain-free on a sample holder 4 of arbitrary design since they require no physical contact with the cold finger for cooling. The sample holder 4 is supported by an insulated rod 19 which passes through O-ring 22 at an upper end of chamber 5 to seal the sample chamber 5. A knob 14 is attached to an end of rod 19 at a point outside the cryostat.

The knob 14 is capable of manipulating the sample holder 4 to be rotateable or moveable in a vertical direction in order to bring selected ones of the samples 3 into view through optical access windows 9 and 17. The inner windows 9 are sealed with indium O-rings to ensure that the sample chamber 5 containing the exchange gas is isolated from the outer, insulating vacuum chamber 6. The outer windows 17 are incorporated into the construction of the chamber 6 by a flange 20 defining a portion of the sidewalls of chamber 6. Advantageously, an operator can easily position the samples 3 by looking through the optical port and manipulating the knob 14.

A vacuum cross 18 serves as an upper end of the sample chamber 5, and is adapted to admit the exchange gas through input port 13 and to couple electrical leads 12 to the sample holder. These electrical leads may connect to a temperature sensing transducer 16 on the bottom of the sample holder 4 for monitoring sample temperatures, or to make direct electrical contact to the samples, such as electronic devices, if necessary for operational purposes.

The cooling of samples 3 occurs as follows. The sample chamber 5 is completely evacuated through inlet 13 in order to prevent frosting in chamber 5 resulting from air freezing at cryogenic temperatures. An appropriate amount of exchange gas, typically at a pressure of a fraction of an atmosphere, is admitted through inlet 13, and the inlet is then closed to seal chamber 5.

Preferably, the gas pressure is strictly controlled in order to prevent upwardly-flowing convection currents from developing in the sample chamber which could reduce the exchange of heat between the samples and copper block. With the appropriate gas pressure, a sufficient density gradient will exist in the sample chamber such that denser cold air remains in the chamber bottom toward the end of the sample where heat exchange occurs.

The exchange gas serves as a thermal carrier means allowing the samples 3 to thermally communicate with block 2, thereby transferring thermal energy between samples 3 and block 2 as long as block 2 is at a lower temperature than the samples. The samples 3 are eventually cooled to cryogenic temperatures since block 2 is maintained at cryogenic temperatures due to its thermal contact with the cold finger.

The rate of cooling may be regulated by controlling the cryopump cooling rate, the sample heat load, the exchange gas pressure, and the relative geometry of the block 2 to the remainder of the chamber 5. An exchange gas with a low freezing point is desirable to avoid frosting and diminished heat transfer at cryogenic temperatures. Accordingly, the gas is preferably helium, but may include argon, although with argon the available cooling temperatures would then be limited to approximately 100K rather than 15K with helium.

Furthermore, the thermal transfer between the samples 3 and block 2 may be enhanced by increasing the inner surface area of block 2 relative to the entire interior surface area of chamber 5. It is desirable to minimize heat transfer through and along the sidewalls of chamber 5 to achieve efficient heat exchange in the sample chamber 5. Accordingly, heat transfer from the exposure to room temperature of area 23 of the chamber 5 sidewall is minimized by constructing chamber 5 to have sidewalls of high thermal resistance. Such thermal resistance exists with thin, elongated sidewalls of stainless steel.

In an assembly built in accordance with the present invention, the diameter of the circular outer chamber 6 was 3", the height of the chamber 6 was approximately 18.5", the diameter of the circular sample chamber was 1.5", and the vertical distance from the upper end 24 to th end 18 is 10".

The cryopump used to cool the cold finger may be a commercially available helium cryopump capable of routinely and easily maintaining temperatures as low as −441° F. (about 15K). Advantageously, the apparatus of the present invention requires no cryoliquids as in conventional immersive cryostats since the cryopump employs a Joule-Thompson cycle to provide a cryogenically-cooled gas for subsequent cooling of the cold finger.

While there has been shown and described what are at present considered the preferred embodiments of the invention, it will be obvious to those skilled in the art that various alterations and modifications may be made therein without departing from the scope of the invention.

What is claimed is:

1. An apparatus for cryogenically cooling a sample, comprising:
    a sample chamber;
    means for suspending the sample within said sample chamber;
    a vacuum chamber enclosing the sample chamber;
    a cryogenic element forming at least part of said sample chamber and being in spaced-apart relation to the sample when said sample is placed in said sample chamber;
    cryopump means for maintaining said element at cryogenic temperatures; and
    means for introducing a sufficient heat-conductive gas at a pressure into the sample chamber to place the sample in thermal communication with the cryogenic element.

2. The apparatus as recited in claim 1 wherein said cryopump means further comprises:
    a gas cryopump with a cold finger in thermal communication with said element.

3. An apparatus for cryogenically cooling a sample, comprising:
    a sample chamber for surrounding said sample and having a port adapted to receive gas;
    a vacuum chamber enclosing said sample chamber for thermally insulating said sample chamber;
    a thermally conductive element forming at least part of said sample chamber and being in spaced-apart relation to said sample when said sample is placed in said sample chamber
    a gas cryopump coupled to said element for maintaining said element at cryogenic temperatures; and
    means coupled to said port for admitting gas into said chamber;
    whereby said gas communicates heat from said sample to said element such that said sample is cryogenically cooled without experiencing strain.

4. The apparatus as recited in claim 3 wherein:
    said gas is helium.

5. An apparatus for operating electronic devices at cryogenic temperatures, comprising:
    a sample chamber;
    means for suspending the devices within said sample chamber;
    a vacuum cross defining an upper end of said sample chamber, and adapted to receive a gas through one port and electrical leads through another port;
    a vacuum chamber enclosing the sample chamber;
    a cryogenic element forming at least part of said sample chamber and in spaced-apart relation to the devices;
    cooling means for maintaining said element at cryogenic temperatures; and
    means coupled to the gas port of said sample chamber for introducing a sufficient heat-conductive gas at a pressure into the sample chamber to place the devices in thermal communication with the cryogenic element;
    electrical leads connected to said devices through said another port; and
    means coupled to said leads for operably driving said devices.

6. A method of cryogenically cooling a sample, comprising the steps of:
    suspending said sample in a sample chamber having a thermally-conductive element exposed to said sample as part of said chamber;
    thermally insulating said sample chamber;
    maintaining said element at cryogenic temperatures with a gas cryopump;
    evacuating said sample chamber;
    admitting gas into said evacuated sample chamber through a gas inlet of said sample chamber; and
    sealing said inlet after a sufficient amount of gas is present in said chamber such that said sample is in thermal communication with said element.

* * * * *